(12) United States Patent
Hill (10) Patent No.: US 8,000,811 B2
(45) Date of Patent: Aug. 16, 2011

(54) SUTURE SLEEVE

(75) Inventor: Rolf Hill, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 792 days.

(21) Appl. No.: 11/997,264

(22) PCT Filed: Aug. 24, 2005

(86) PCT No.: PCT/SE2005/001237
§ 371 (c)(1),
(2), (4) Date: Jan. 29, 2008

(87) PCT Pub. No.: WO2007/024164
PCT Pub. Date: Mar. 1, 2007

(65) Prior Publication Data
US 2008/0228251 A1  Sep. 18, 2008

(51) Int. Cl.
*A61N 1/00* (2006.01)
(52) U.S. Cl. .................................................. 607/132
(58) Field of Classification Search ................. 604/174; 607/132; 606/151
See application file for complete search history.

(56) References Cited

U.S. PATENT DOCUMENTS

| | | | |
|---|---|---|---|
| 5,273,053 A | 12/1993 | Pohndorf | |
| 5,603,730 A | 2/1997 | Romkee | |
| 5,683,403 A | 11/1997 | Adams et al. | |
| 5,746,722 A | 5/1998 | Pohndorf et al. | |
| 5,843,146 A | 12/1998 | Cross, Jr. | |
| 5,957,968 A | 9/1999 | Belden et al. | |
| 6,473,654 B1 | 10/2002 | Chinn | |
| 2004/0254623 A1 | 12/2004 | Rodriguez et al. | |

FOREIGN PATENT DOCUMENTS

| | | |
|---|---|---|
| EP | 0 597 213 | 5/1994 |
| EP | 0 625 359 | 11/1994 |

OTHER PUBLICATIONS

"Experience With A Lead Fixation/Suture Sleeve," Gammage et al, PACE, vol. 21 (1998) pp. 459-552.

*Primary Examiner* — Scott Getzow
(74) *Attorney, Agent, or Firm* — Schiff Hardin LLP (57) ABSTRACT

A suture sleeve for securing an implantable lead to body tissue has a lumen that receives the lead and that includes a locking arrangement that secures the sleeve at a selected position along the lead. The locking arrangement provides the suture sleeve with three modes of operation. In the first mode, the size of the lumen exceeds the diameter of the lead, such that the suture sleeve is easily movable along the lead. In the second mode, the size of at least a portion of the lumen is reduced, causing the sleeve to apply pressure to the lead so that relative movement between the sleeve and the lead is prevented. In the third mode, the pressure is temporarily released, allowing the sleeve to again be movable along the lead.

13 Claims, 4 Drawing Sheets

SUTURE SLEEVE

BACKGROUND OF THE INVENTION

1. Field of the Invention

The present invention generally relates to the field of implantable medical devices. More specifically, the present invention relates to a suture sleeve for securing an implantable lead to body tissue.

2. Description of the Prior Art

Suture sleeves are used for securing a lead to a patient's body tissue, for instance a lead used for electrical connection between a heart stimulator, e.g. a pacemaker, and a heart. The purpose of the suture sleeve is to provide an aid for suturing and fixating the lead at a desired position in the body, which in the field of heart stimulators generally is at the point of entry into a vein. Thus, the suture sleeve is arranged to fixate the sleeve at a selected position along the lead, and often presents a guiding groove, or the like, into which the suture can be tied.

U.S. Pat. No. 5,273,053 discloses a suture sleeve, which is adapted to secure a lead to a patient's body tissue. The suture sleeve comprises a sleeve body, which has a longitudinal through bore to receive the lead and a perpendicular channel intersecting the longitudinal through bore, and a pushbutton lock member. The pushbutton lock member is movable within the perpendicular channel and has a through bore dimensioned to receive the lead. Further, the pushbutton lock member may upon depression of the lock member be moved laterally from a first position, in which the lead may run freely within the sleeve, to a second position, in which the lead is fixed in position in relation to the sleeve. In order for the lock member to release the lead to move freely within the sleeve, the lock member must be returned to the first position be pressing the opposite side of the lock member, which may be a delicate and difficult operation, especially when the sleeve and lead are positioned inside the body during implantation.

U.S. Pat. No. 5,603,730 discloses another example of a suture sleeve. The sleeve has an elongated body which defines a bore and is provided with a relief aperture at a first intermediate position on the body and communicating with the bore. Said sleeve includes a pair of actuator tabs attached at a second intermediate position on the body and extending laterally therefrom. At least a portion of the relief aperture is positioned between the tabs such that actuation of the tabs causes enlargement of the aperture. The sleeve is movable between a tighter state, in which a lead passing through the bore does not readily slide longitudinally within the bore, and a looser state, in which the lead may slide readily through the bore. Thus, the actuator tabs must be continuously manipulated when the sleeve is to be moved along the lead.

Currently, the technological development within the field of heart stimulators is moving towards thinner and thinner leads. This puts higher demands on the properties of the suture sleeve in order to meet the requirements of ever thinner leads, in terms of safe and convenient handling of the sleeve and avoiding the risk of suture tie-down damages to the lead.

SUMMARY OF THE INVENTION

An object of the present invention is to mitigate at least some of the drawbacks of the prior art.

According to an aspect of the present invention, there is provided a suture sleeve for securing an implantable lead to body tissue, the implantable lead having an outer lead diameter, having a first tubular portion, having a lumen arranged for receiving said implantable lead. The first tubular portion has a locking arrangement for securing the suture sleeve at a position along the lead. The locking arrangement provides the suture sleeve with three modes of operation. In a first mode, the transversal size of the lumen exceeds the lead diameter, such that the suture sleeve is easily moveable along the lead. In a second mode, the transversal size of at least a portion of the lumen is reduced, whereby the first tubular portion applies a pressure onto the lead, such that the suture sleeve is prevented from moving along the lead. In a third mode, the pressure is temporarily released, such that the suture sleeve can be moved along the lead. A transition from the first mode to the second mode is provided by the locking arrangement in a first manner and a transition between the second mode and the third mode is provided by the locking arrangement in a second manner, which is different from the first manner.

Thus, the present invention is based on the idea of providing a suture sleeve with three modes of operation. In the first mode, the transversal size of the lumen of said tubular portion exceeds the outer diameter of the lead, such that the suture sleeve is easily moveable along the lead. This mode is used by a surgeon before and during implantation. Firstly, before implantation, the suture sleeve may need to be mounted onto the lead, e.g. by insertion of the lead into the sleeve, which requires the inner dimensions of the tubular sleeve to be larger than the outer diameter of the lead. Secondly, during implantation, when the surgeon determines where the lead shall be positioned, the procedure may be considerably facilitated if the sleeve may be freely and easily moved along the lead. In particular if the sleeve does not require to be actively manipulated for increasing the inner diameter of the sleeve in order to make it movable, while the sleeve is simultaneously moved to the desired position on the lead. It should be noted that the step of mounting the suture sleeve onto the lead could already have been performed when the surgeon receives the lead for implantation.

In the second mode, the transversal size of at least a portion of the lumen of the first tubular portion is reduced. Thereby, portions of the suture sleeve applies pressure onto the lead, such that the suture sleeve is prevented from moving along the lead. A fixed position of the sleeve on the lead, facilitates implantation and suturing of the sleeve. When a surgeon during implantation has selected an appropriate position for the sleeve along the lead, the surgeon manipulates the sleeve in order to fixate the selected position. Thus, the suture sleeve maintains its position along the lead during the phase of implantation when the suture sleeve, and thereby the lead, is sutured to body tissue. After implantation, the suture sleeve remains in the second mode and the specific position, selected during implantation, is maintained by the suture sleeve.

Furthermore, in the third mode of operation, the pressure applied by the first tubular portion is temporarily increased, such that the suture sleeve can be moved along the lead. When an operator, such as a surgeon, during implantation needs to adjust the position of the suture sleeve, the operator temporarily manipulates the sleeve to release the pressure retaining the sleeve at a specific location on the lead, and moves the sleeve along the lead. As soon as the operator ceases to actuate the sleeve, it returns to its second mode of operation.

Thus, the sleeve in the first mode may be easily handled by an operator to be passed onto and moved along a lead, in the second mode securely retain a selected position on a lead, and in the third mode be manipulated to be moved and repositioned along the lead. Consequently, there are two transitions between the three modes of operation, a first transition between the first and second modes of operation, and a second transition between the second and third modes of operation. The locking arrangement is arranged to provide, when manipulated, the first transition in a first manner, and the second transition in a second manner, different from the first manner. Thus, even though the operator may manipulate the sleeve in similar manner for changing from the first to the second mode as for changing from the second to the third mode, such as by depressing or compressing portions of the sleeve, the locking arrangement is arranged to perform the respective transitions in different manners. In some embodiments of the invention, the locking arrangement has a first component that provides the first transition and a second component that provides the second transition. However, the same elements can be provided for providing both transitions, although having two different manners of operation for the two different transitions.

As mentioned above, the suture sleeve has a tube or tubular portion, having a lumen into which the lead is introduced. The implantable lead has a certain lead diameter, which can vary between different types of leads, to which the size of said lumen is adapted. The inner dimensions of the lumen are in the first mode adapted such that the sleeve is easily movable along the lead. The tubular portion comprises a locking arrangement for securing the suture sleeve at a position along the lead, wherein the locking arrangement is arranged to provide the suture sleeve with three modes of operation, as explained above.

Furthermore, according to embodiments of the invention, the suture sleeve, and in particular the locking arrangement thereof, may be unbiased in the first mode of operation, and the sleeve is freely movable along the lead. In the second mode of operation, the locking arrangement of the sleeve is biased and at least one engagement element applies pressure onto the outer surface of the lead. In the third mode of operation, the pressure applied by the engagement element(s) on the lead is reduced or removed. Hence, it may be sufficient that the pressure exerted by the engagement element onto the lead is reduced, in order for an operator to be able to move the suture sleeve along the lead. Furthermore, the suture sleeve will not remain in the third mode, unless it is actively operated to remain in the third mode. Hence, the third mode is active only when manipulated by the operator and the suture sleeve returns to the second mode when the operator stops actuating the locking arrangement of the sleeve. Also) the second mode can be regarded as a state of equilibrium and, consequently, no actions are required by the operator to allow the suture sleeve to remain in the second mode. The first mode can also be regarded as a state of equilibrium, since the sleeve does not have to be manipulated in order to remain in the first mode of operation.

In embodiments of the invention, the locking arrangement has a retainer, arranged to be operable in an engaged state and in a temporarily released state. In the first mode of operation, the retainer is not in engagement with the lead, and the sleeve may run freely in relation to the lead, and vice versa. In the second mode of operation of the suture sleeve, the retainer is operated in the engaged state, such that the retainer is brought into engagement with the lead and retains the suture sleeve at a position along the lead, preferably by means of frictional force. In the third mode of operation of the suture sleeve, the retainer is operated in the temporarily released state. In this state, the retainer allows the operator to reposition the sleeve at another position along the lead.

Furthermore, the retainer can in some embodiments include at least one leverage arrangement having an engagement element and a manipulating element connected via a pivot point. In the engaged state, the engagement element applies a pressure on the lead for securing the suture sleeve at a position along the lead. In the temporarily released state, the manipulating element is handled by an operator such as a surgeon, which applies pressure on the manipulating element. When the surgeon puts pressure on the manipulation element, the engagement element will release the pressure onto the lead. Thereby, the surgeon may release the retainer using only one hand, possibly even using only two fingers, which facilitates the repositioning of the suture sleeve along the lead during the implantation procedure. In this embodiment, the control of the engagement element via the manipulating element is achieved by means of a leverage effect. When the pressure exerted by the suture sleeve onto the surface of the lead is released, the sleeve may be moved along the lead.

The leverage arrangement(s) can include a number of engagement elements connected to the manipulating element via one or more pivot points. Thereby, several points of engagement between the suture sleeve and the lead can be provided. By applying more engagement elements, or rather points of pressure between the sleeve and the lead, the fixation of the sleeve on the lead may be improved. Furthermore, a reduced pressure is then required from each engagement element, which reduces the risk of damage to the lead surface.

In embodiments of the invention, the outer portion of the suture sleeve is provided with markings or indications where the suture sleeve is to be manipulated in order to achieve the transitions between the different modes of operation, i.e. to actuate the locking arrangement of the sleeve. In the embodiments referred to above, in which a manipulating element is provided for actuating engagement elements, the longitudinal, and possibly also the circumferential, position of the manipulating element is preferably indicated on the outer surface of the sleeve. For instance, an indentation, notch or recess can be provided where pressure is to be applied in order to actuate the locking arrangement. The indication can also be in the form of an unevenness or small projection on the surface, or any other easily discernible indication. Preferably, the indication is easily discernible by the surgeon using only the feel of his hands.

In some embodiments of the suture sleeve according to the invention, the locking arrangement comprises a snap lock, which is arranged to be operable in an open state in connection with the first mode of operation, and in a closed state in connection with the second and third modes of operation. Thus, during implantation, the snap lock is open for the sleeve to be freely moved along the lead. As soon as the surgeon has decided where on the lead the sleeve should be positioned, the snap lock is actuated, i.e. locked, such the selected position may be maintained. The snap lock is arranged to prevent a transition from the second, and also the third, mode of operation to the first mode of operation, i.e. the open state. Thus, after implantation, the suture sleeve is only intended to be reversibly operable between the second and third modes of operation, unless the biasing generated in said second mode is neutralized by the operator opening (or disengaging) the snap lock.

Additionally, the suture sleeve may on the outer surface thereof be provided with at least one circumferential groove, which is adapted to receive a suture. Such a circumferential groove will guide the suture and prevent the suture from sliding off the suture sleeve. In exemplifying embodiments of the invention, two circumferential grooves are provided, one at each end of the sleeve. However, a sleeve having only one circumferential groove is also possible in this embodiment. Furthermore, the term "groove" should be interpreted in a wide sense. Other forms of a recess, or the like, in which a suture can come into engagement with and be secured to the sleeve are also contemplated within the scope of the present invention. Also, even though it may be a suitable feature, the invention is not restricted to sleeves comprising grooves for securing sutures.

In further embodiments of the invention, and related to the embodiment described above where the suture sleeve has engagement elements for providing pressure onto the lead surface, said at least one circumferential groove may be positioned circumferentially of said engagement element. Thereby, the applied suture may provide additional pressure onto the engagement element, which improves the fixation of the suture sleeve at a position along the lead. Thus, after the sleeve and lead have been sutured to body tissue, the suture may provide radial pressure onto the surface of the suture sleeve. Since, in this embodiment, the longitudinal positions of the suture grooves are aligned with the engagement elements of the retaining means, the engagement elements are then pressed radially towards the, lead surface.

Also, the suture will prevent the pressure applied by the engagement elements against the lead to be temporarily released. Thus, even if the suture sleeve is manipulated to enter the third mode, where the sleeve can be moved along the lead, the positions of the engagement elements will be fixedly maintained by the pressure of the suture and the engagement elements will continue to be in engagement against the lead.

Furthermore, the suture sleeve may be arranged for limiting the radial movement of the engagement elements towards the lead, in order to protect the lead from damage when added pressure is applied by sutures. For instance, the tube may be given an essentially circular circumference, broken only where the engagement elements are arranged. The suture would then be applied circumferentially around portions of the tube with the outer surface of the engagement elements, which can be displaced by the suture, and the remaining circular surface of the tube, which can not be displaced by the suture. Thus, the circumferential width of the outer surface of the engagement elements, i.e. in the direction towards an applied suture, would then restrict how much the engagement elements can be displaced in the radial direction towards the lead. This will be more clear in the following description with reference to the accompanying drawings.

In embodiments of the suture sleeve according to the present invention, the first tubular portion is made of a rigid material. Thereby, the lead may be protected from cutting damages by the scalpel of a surgeon, for instance if the vein has to be opened for re-positioning or resuturing of the lead or the suture sleeve, or when the suture sleeve is to be removed from the lead.

Furthermore, a rigid tube is also beneficial for withstanding suture tie-down damages. Then, according to further embodiments of the suture sleeve, the lumen of the first tubular portion can be provided with a minimum transversal size, preferably a minimum diameter, in the second and third modes of operation.

In further exemplifying embodiments of the present invention, the suture sleeve has a second tubular portion having a lumen for receiving and enclosing the first tubular portion. Thus, the suture sleeve is comprised by at least two separate components, which are preferably assembled together before mounting the sleeve onto the implantable lead. The provision of two tubular elements provides a number of advantages. The design of the inner tubular portion can be adapted solely to the implantable lead, without concern for surrounding tissue, apart from making the inner portion from a material suitable for the environment inside a human body. Likewise, the outer tubular portion can be adapted to the surrounding tissue and to the suturing of the sleeve to body tissue.

The outer tubular portion may be made in a flexible or soft material, such that the risk of the suture sleeve damaging surrounding tissue is reduced. Furthermore, by providing the outer portion in a flexible material, the pressure applied by the suture may be transmitted by the flexible outer tube to the inner tube, in particular to the engagement elements of the inner tube in accordance with the embodiments described above.

The flexible material of the outer portion may also be suitable for easy removal by a scalpel such that the inner tube may be accessed. Then, the inner tube is suitably rigid such that the risk of damaging the lead when using a scalpel is significantly reduced. When the outer tube has been removed, the locking arrangement of the inner tube can be accessed by the surgeon.

In the embodiments referred to above where an actuation indicator is provided in the surface of the sleeve, where inner and outer tubes are provided, the indicator is provided on the outer tube. This is further elucidated in the ensuing description with reference to the accompanying drawings.

In the embodiments where two tubular portions are used, the outer surface of the second, outer tubular portion may be provided with the circumferential groove(s) of the embodiments described above.

Moreover, the length of a flexible outer tubular portion of the suture sleeve may exceed the length of the inner tubular portion, in particular if the inner portion is made from a rigid material. Then, a bend of the implantable lead adjacent to the sleeve, whether desirable or not, would not result in the surface of the lead rubbing against a rigid edge of the sleeve. Instead, the ends of the inner tubular portion would flexibly support the lead and protect it from possible failure.

Furthermore, the suture sleeve may be provided with a longitudinal slit, which is arranged to act as a cutting guide during removal of the suture sleeve from the lead. This will facilitate the cutting open of the tubular portion, if required, since the movement of a scalpel will be guided by the slit and the risk of the scalpel "sliding off" the tube and damaging surrounding tissue or the lead is reduced. This is particularly suitable in the embodiments with outer and inner tubular portions. Then, the longitudinal slit is provided on the outer surface of the outer tube, which preferably is made in a flexible material.

DESCRIPTION OF THE PREFERRED EMBODIMENTS

The following is a description of exemplifying embodiments in accordance with the present invention. This description is intended for describing the general principles of the invention and is not to be taken in a limiting sense. Thus, even though a suture sleeve comprising separable outer and inner portions is illustrated, the scope of the invention includes suture sleeves constituted by one tubular portion. Furthermore, even though the illustrated locking arrangement comprises two means for performing the transitions between the three different modes of operation, a single means for performing the transitions, although in two different manners, is contemplated within the scope of the invention.

Figure 1:
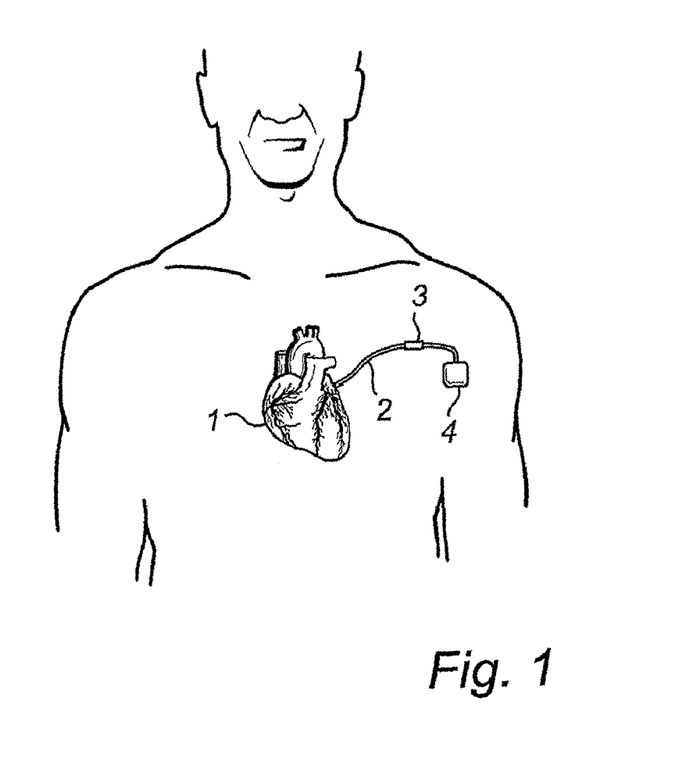
FIG. 1 is a schematical view of a patient's body showing an implantable heart stimulator, a lead, a suture sleeve and a heart.

Referring first to FIG. 1, there is shown an implantable heart stimulator 4' when implanted in a patient's body. A lead 2 connects the heart stimulator 4 to the heart 1, thereby allowing stimulation of the heart 1 and control of the heart rhythm. A suture sleeve 3 is provided at a position along the lead 2 in order to fixate the position of the lead 2 in the body.

Figure 2:
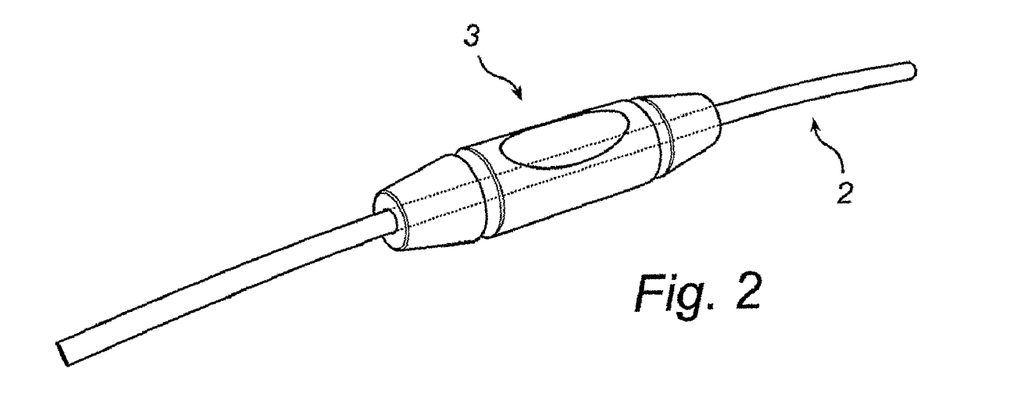
FIG. 2 is a perspective view of a suture sleeve arranged at a position along a lead.

In FIG. 2, there is shown an enlarged view of a suture sleeve 3 arranged at a position along a lead 2. It can be seen that the inner diameter of the suture sleeve is adapted to the outer diameter of the lead 2.

Figure 3:
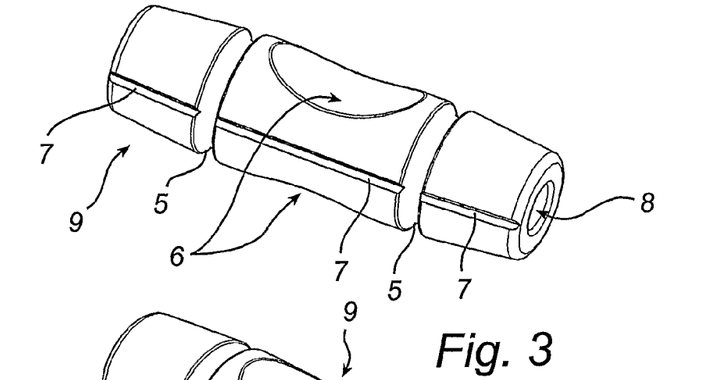
FIG. 3 is a perspective view of the outer tubular portion.

Now referring to FIG. 3, there is presented a perspective view of the outer tubular portion or tube 9, having a lumen 8 for receiving an inner tubular portion or tube 10. The outer tubular portion 9 comprises, in this example, two circumferential grooves 5, two actuation areas 6, which are located on opposite sides of the outer tubular portion 9, and a longitudinal slit 7. The circumferential grooves 5 are intended for engagement with suture wires when suturing the sleeve 3 to body tissue. The grooves 5 improve the grip of the suture on the suture sleeve and prevents the suture from sliding off the sleeve during and after suture. The actuation areas 6 are provided with indentations acting as indicators and provide guiding for where pressure should be exerted in order to actuate the transition between the different modes of operation. The longitudinal slit 7 indicates where to cut, if or when the suture sleeve is to be removed.

Particularly, the outer portion is made of a flexible material, such as silicone or any other equivalent material, that allows the inner diameter of the outer portion to be expanded, while the inner portion, with a outer diameter that is slightly larger than the inner diameter of the outer portion, is inserted. The outer tubular portion may be used in conjunction with a variety of inner tubular or core portions, of which two examples are described. It is to be understood that other working examples of the inner core portions are contemplated. Even though they are not described here, they nevertheless fall within the scope of the invention as claimed in the appended claims.

Figures 4, 5, 6, 7:
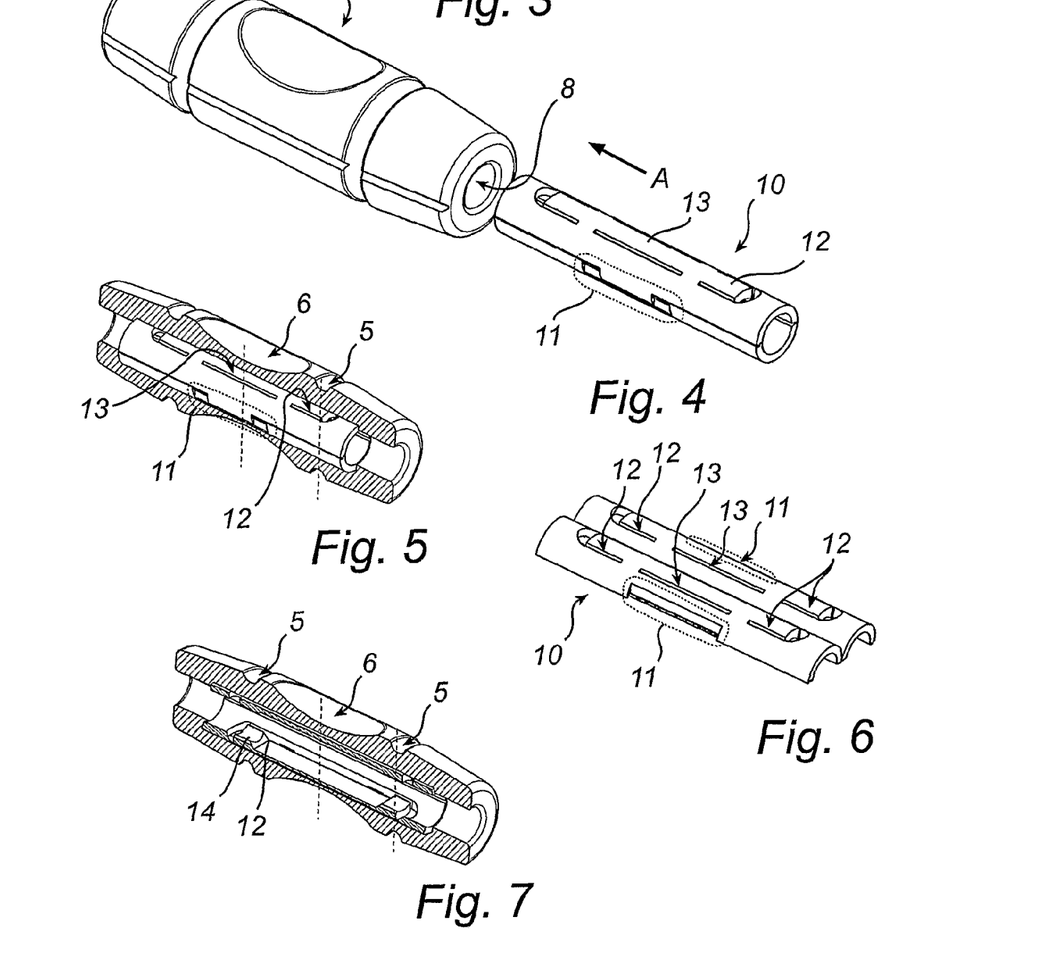
FIG. 4 is a perspective view of the outer tubular portion and an inner tubular portion.
FIG. 5 is a partly cut-away view of the inner tubular portion when mounted into the outer tubular portion.
FIG. 6 is a perspective view of the inner tubular portion when the snap locking mechanism is open.
FIG. 7 is a cross-sectional view of the assembled outer and inner tubular portions.

In FIG. 4, there is indicated a perspective view of the outer tubular portion 9 and a first exemplifying illustration of an inner core portion 10, wherein the inner core portion 10 is intended to be inserted into the lumen 8 of the outer tubular portion 9 according to arrow A. Note that the inner diameter of the end portions of the flexible outer tubular portion 9, respectively, is slightly smaller than the outer diameter of the inner core portion 10.

The inner core portion 10, or inner tube, is made from two essentially semi-cylindrical portions which are connected via a hinge mechanism (not shown). The core portion 10 comprises a snap locking mechanism 11 for securing and closing the two semi-cylindrical portions into the general shape of a cylindrical tube. The inner core portion 10 further comprises a retaining mechanism for retaining the sleeve at a selected position along the lead. The retaining mechanism comprises a depressible manipulating portion 13 and engagement elements 12, to be described in further detail below. The entire core portion 10 is made as a one-piece structure.

With reference to FIG. 5, it is demonstrated how the diameter of the outer tubular portion fits to the diameter of the inner portion, such that a snug fit is provided. It can also be seen that the depression 6 of the outer tubular portion 9 is aligned with the depressible portion 13 of the inner portion 10, as well as with the snap locking mechanism 11. In particular, the locations of the circumferential grooves 5 matches the location of the engagement elements 12 of the inner portion 10, such that, when sutured, the elements 12 are held against the lead even though a pressure would be exerted onto the depressible portion 13. When the outer and inner portions are arranged according to FIG. 5, the suture sleeve has been completely assembled and is ready for operation.

In FIG. 6, the snap lock 11 of the inner core portion 10 is depicted in a perspective view. As can be seen in the figure, the snap lock 11 is shown in an open state, whereby the entire inner core portion 10 may be opened such that the lead can be removed after the outer tubular portion has been cut open and removed. Furthermore, following assembly of the inner and outer portions 9, 10, but prior to or during fitting of the suture sleeve 3 onto the implantable lead 2, the snap locking mechanism 11 is in an open or a semi-open state. In the open state of the snap lock, the outer tube 9 prevents the inner tube 10 from opening up altogether. However, the snap lock 11 of the inner tube 10 is preferably in a semi-open state in which the opposing portions of the snap lock 11 are in engagement, but where the snap lock 11 may be further closed when pressure is applied to the suture sleeve. In other words, the snap lock 11 may be provided with a plurality snap catches, such that the inner tubular portion 10 may be closed in steps. Then, the first step would provide the inner tubular portion 10 with such inner dimensions that it would still be freely movable along the lead.

The retaining mechanism, as illustrated in FIGS. 6 and 7, comprises engagement elements 12 having projections 14, that protrude into the lumen of the inner core portion 10, and a depressible portion 13. The depressible portion 13 of the manipulating element is located centrally with regard to the longitudinal direction of the inner tubular portion 10, and is connected to the engagement elements 12 via a respective pivot point. Thus, the inner tubular portion is operable to loosen the grip on the lead by means of a leverage effect upon applying pressure on the depressible portion 13.

Turning now to the cross-sectional view of the inner core portion and the outer tubular portion, as shown in FIG. 7, note how the depression of the outer tubular portion matches the depressible portion of the inner core portion. It can also be noted how the circumferential grooves 5 are aligned with the projections 14, such that the engagement elements 12, and the projections 14 thereof, can be displaced towards the lead when pressure is applied by a suture that is tied down in the suture grooves 5. As readily understood from FIGS. 6 and 7, the projections 12 can only be displaced a limited distance, due to the geometrical configuration of the retaining mechanism and the adjacent portion of the cylindrical tube. Thereby, the lead is protected from tie down failure.

Figure 8A:
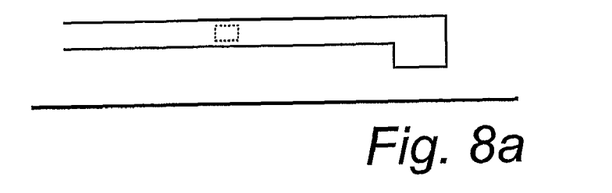
FIGS. 8A through 8C are cross-sectional side views illustrating the function of the engagement elements in an embodiment of the invention.
Figure 8B:
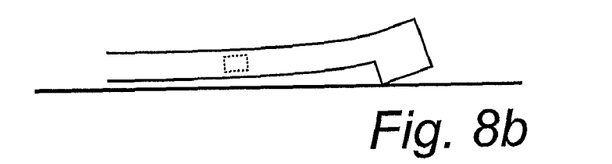
Figure 8C:
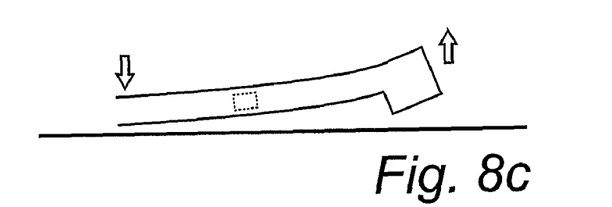

FIGS. 8A through 8C demonstrate in greater detail the function of the engagement elements 12. In FIG. 8A, the situation when the suture sleeve is in the first mode is illustrated. Then, the snap lock 11 is in the open state, wherein the suture sleeve is easily movable along the lead. In this first mode, the retaining mechanism is unbiased, and there is essentially no contact between the retaining elements and the surface of the lead.

In FIG. 8B, a transition has been made such that the suture sleeve is in the second mode. Here, the snap lock 11 is in the closed state and the retainer is in the engaged state, wherein the suture sleeve is fixed at a position along the lead. The projection of the retaining mechanism has been displaced radially inwardly and is pressed radially outwardly by the lead surface. Thus, the engagement element is biased against the lead and the projection exerts a pressure onto said lead.

In FIG. 8C, there is illustrated the situation when the suture sleeve is in the third mode. Now, the snap lock is in the closed state and the retainer is in the temporarily released state, wherein the pressure exerted by the projection 12 is temporarily released from the lead such that the suture sleeve can be moved along the lead. For illustrative purposes, a gap has been provided between the projection and the lead. This is, however, not required. It may be sufficient to decrease the pressure exerted onto the lead by means of applying pressing onto the depressible area 13, which by a leverage effect acts on the projection 12, in order for the sleeve to be movable along the lead.

Figure 9:
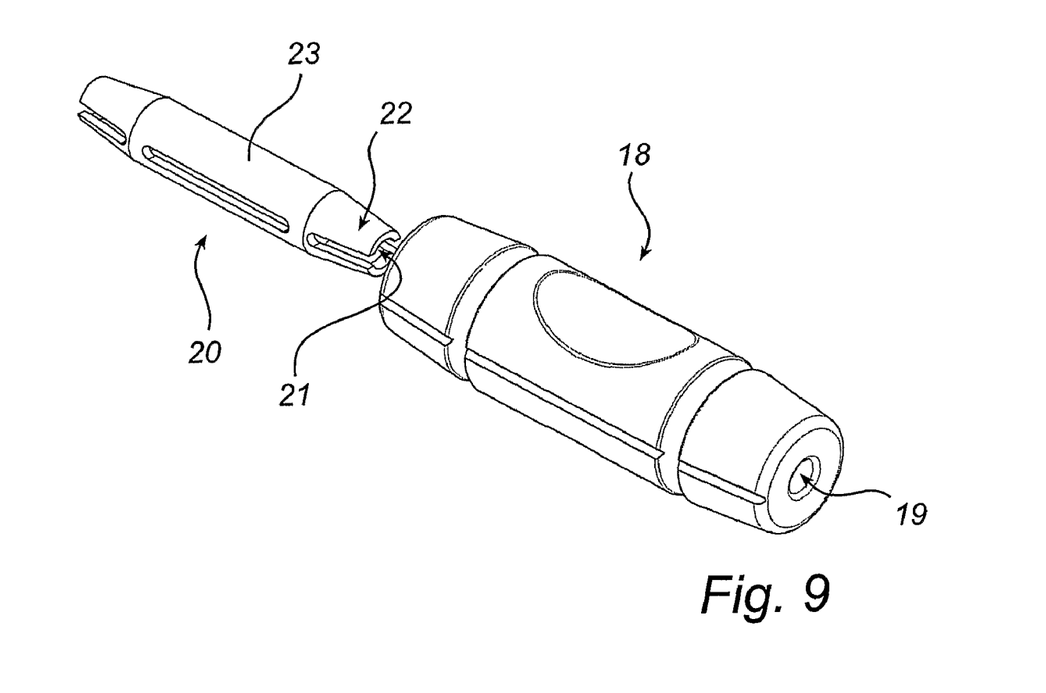
FIG. 9 is a perspective view of a further embodiment of the invention.
Figure 10:
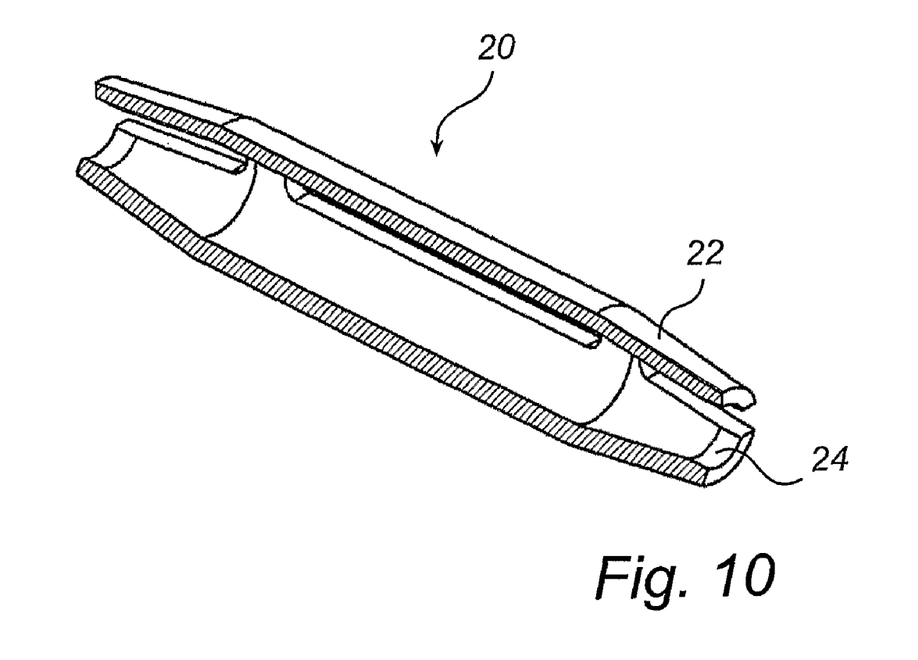
FIG. 10 is a cross-sectional view of the inner portion of FIG. 9.
Figure 11:
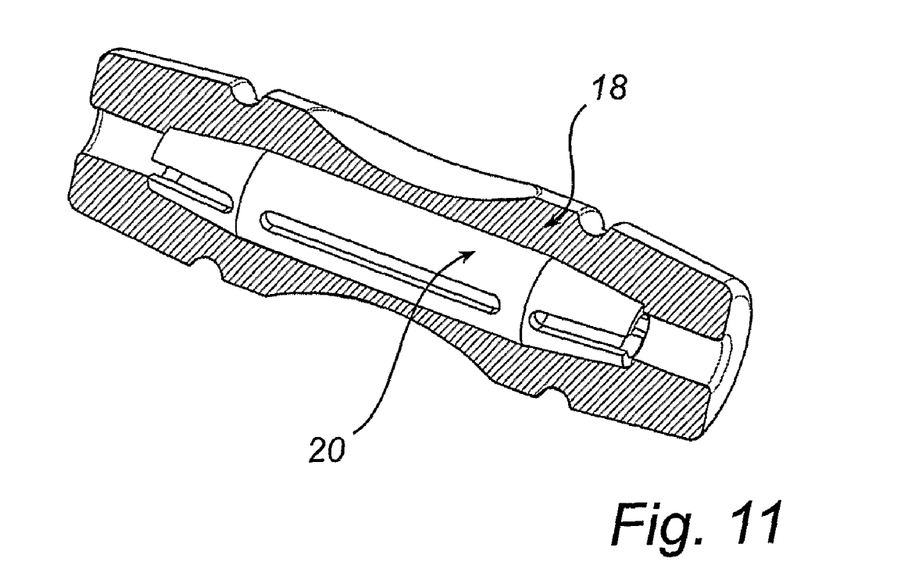
FIG. 11 is a partly cut-away view of the inner tubular portion, according to FIGS. 9 and 10, when mounted into the outer tubular portion.

In a second working example, shown in FIGS. 9 through 11, there is provided another example of an inner core portion 20 and an outer tubular portion 18. The inner core portion 20 operates according to the same basic principles as the previously described inner portion. The inner core portion 20 depicted in FIG. 9 comprises a centrally arranged depressible area 23 and distally arranged engagement elements 22, at a longitudinal end of the inner portion, respectively. Projections 24 of the engagement elements 22 protrude into the lumen 21 of the inner portion 20 and are arranged to be brought into engagement with the outer surface of an implantable lead. In the described example, the cross sections of the projections 24 are in the form of circular arcs, such that a smooth and large contact surface can be obtained between the projections 24 and the surface of the lead. The engagement elements 22 are further connected to the depressible portion via pivot points, respectively, such that the depressible portion 23 is operable to loosen the grip on the lead by means of a leverage effect. The inner core portion according to this embodiment further comprises a snap locking mechanism (not shown) similar to that of the inner core portion 10 in the embodiment described above.

The outer tubular portion 18 differs only with respect to the shape of the lumen 19 from the lumen 8 of the previously mentioned outer tubular portion 9. The exterior of the outer tubular portions 9, 18 are in these examples similar. In all other aspects, the outer tubular portion 9 of this embodiment is operated in a similar manner as described above. It is to be noted that the suture grooves may also in this working example match the position of the engagement point(s) of the projections. Likewise, the snap lock 11 may be matched by the actuation areas, which provide guiding for the operator.

Referring to FIG. 10, there is provided a cross-sectional view of the inner portion 20 in its unbiased state. In this embodiment, the inner minimum diameter of the inner portion is less than the diameter of the lead, such that the inner portion 20 will be biased when a lead is inserted into the lumen of the inner portion 20, as is depicted in FIG. 11.

Even though the invention has been described with reference to specific examples thereof, many different alterations, modifications and the like will become apparent for those skilled in the art. The described examples are therefore not intended to limit the scope of the invention, as defined by the appended claims.

I claim as my invention:

1. A suture sleeve for securing an implantable lead to body tissue, said implantable lead having an outer lead diameter, said suture sleeve comprising:

a tubular portion having a lumen therein configured to receive said implantable lead, said tubular portion comprising a locking arrangement allowing said tubular portion to be secured at a position along a length of said implantable lead;

said locking arrangement comprising a manually operable actuating assembly that, when manually actuated, causes said locking arrangement to transition from a first mode that causes a transverse size of said lumen to exceed said outer lead diameter to allow said tubular portion to be movable along said implantable lead, to a second mode that reduces the transverse size of a portion of said lumen to mechanically bias said tubular portion to apply a pressure to said implantable lead that prevents said tubular portion from moving along said implantable lead, and to transition from said second mode to a third mode that temporarily releases bias and thus said pressure to again allow the tubular portion to move along the implantable lead, said locking arrangement being structurally configured to automatically return to said second mode from said third mode unless said actuating assembly is manually activated to maintain said bias to cause said locking arrangement to remain in said third mode; and said locking arrangement comprising a first transition structure that transitions operation of said locking arrangement between said first mode and said second mode, and a second transition structure, different from said first transition structure, that transitions operation of said locking arrangement between said second mode and said third mode.

2. A suture sleeve as claimed in claim 1 wherein said locking arrangement comprises a retainer that is operable in an engaged state wherein said retainer engages said implantable lead and holds said tubular portion at a fixed position relative to said implantable lead when said locking arrangement is operated in said second mode, and that is also operable in a temporarily released state wherein said retainer is disengaged from said implantable lead when said locking arrangement is operated in said third mode.

3. A suture sleeve as claimed in claim 2 wherein said retainer comprises a leverage arrangement comprising an engagement element and a manipulating element connected to said engagement element via a pivot point, said engagement element, in said engaged state of said retainer, applying pressure on said implantable lead that secures said tubular portion at a position along said implantable lead by applying said pressure at said position, and wherein said manipulating element is configured for manual manipulation to release said pressure applied by said engagement element when said retainer is in said temporarily released state, to allow said tubular portion to move along said implantable lead.

4. A suture sleeve as claimed in claim 3 wherein said engagement element is unbiased in said first mode of operation, allowing said tubular portion to move along said implantable lead, and wherein said engagement element is biased to apply said pressure on said implantable lead in said second mode of operation, and wherein the pressure applied by said engagement element on said implantable lead is reduced or removed in said third mode of operation by a lever action at said pivot point between said manipulating element and said engagement element.

5. A suture sleeve as claimed in claim 3 wherein said leverage arrangement comprises a further engagement element connected to said manipulating element via a further pivot point.

6. A suture sleeve as claimed in claim in claim 3 comprising a sleeve housing connected to an exterior of said tubular portion and being co-movable therewith, said sleeve housing having a sleeve housing exterior with a circumferential groove therein into which said engagement element projects, said circumferential groove being configured to receive a suture therein, said suture, when received in said circumferential groove, acting on said engagement element to apply said pressure on said implantable lead to secure said tubular portion and said exterior sleeve at said position along said implantable lead.

7. A suture sleeve as claimed in claim 2 wherein said locking arrangement comprises a snap lock operable in an open state in said first mode and in a closed state in said second mode and in said third mode, said snap lock preventing a change from the closed state to the open state when said locking mechanism is in said second mode and in said third mode.

8. A suture sleeve as claimed in claim 1 wherein said tubular portion is comprised of rigid material.

9. A suture sleeve as claimed in claim 8 wherein said tubular portion has a minimum transverse size in said second mode and in said third mode that protects said implantable lead from breakage.

10. A suture sleeve as claimed in claim 1 comprising a sleeve housing surrounding an exterior of said tubular portion and being co-movable therewith along said implantable lead, said sleeve housing having a sleeve housing exterior with a circumferential groove therein configured to receive a suture.

11. A suture sleeve as claimed in claim 10 wherein said sleeve housing exterior further comprises a longitudinal slit forming a cutting guide facilitating removal of said tubular portion and said sleeve housing from said implantable lead.

12. A suture sleeve as claimed in claim 10 wherein said tubular portion is a first tubular portion, and wherein said sleeve housing forms a second tubular portion concentric with said first tubular portion.

13. A suture sleeve as claimed in claim 12 wherein said second tubular portion is flexible.

* * * * *